United States Patent [19]

Dunmyre et al.

[11] Patent Number: 5,243,864
[45] Date of Patent: Sep. 14, 1993

[54] DEVICE FOR COLLECTING AIRBORNE PARTICULATE SAMPLES

[75] Inventors: George R. Dunmyre; Carol F. Hagerty, both of Murrysville; Xu Li, Pittsburgh, all of Pa.

[73] Assignee: R.J. Lee Group, Inc., Monroeville, Pa.

[21] Appl. No.: 745,686

[22] Filed: Aug. 16, 1991

[51] Int. Cl.$^5$ .............................................. G01N 1/04
[52] U.S. Cl. .................................................... 73/864.71
[58] Field of Search ................ 73/863, 863.21, 863.22, 73/863.23, 864.71, 864.91; 55/270; 356/38

[56] References Cited

U.S. PATENT DOCUMENTS

| | | | |
|---|---|---|---|
| 3,966,474 | 6/1976 | Harper | 430/28 |
| 4,142,576 | 3/1979 | Perry et al. | 165/104.14 |
| 4,144,760 | 3/1979 | Schlueter et al. | 73/425 |
| 4,219,599 | 8/1980 | Idelson et al. | 428/500 |
| 5,012,681 | 5/1991 | Lentzen | 73/863.23 |

FOREIGN PATENT DOCUMENTS 2255822 7/1975 France ............... 73/863.21

Primary Examiner—Robert Raevis
Attorney, Agent, or Firm—Webb, Burden, Ziesenheim & Webb

[57] ABSTRACT

A collection device in which the particle collection surface, tacky due to the presence of aqueous polyvinyl alcohol thereon, is periodically or continually hydrated, rehydrated or replenished. This perpetuated hydration of the polyvinyl alcohol collection surface maintains particle collection effectiveness which would be reduced upon dehydration of the aqueous polyvinyl alcohol to a nontacky anhydrous polymer. In one preferred embodiment of the invention, the collection surface is kept in continuous saturation with aqueous polyvinyl alcohol by means of a wick connecting the collection surface and a reservoir of aqueous polyvinyl alcohol. Other hydration arrangements are included within the scope of the invention. The polyvinyl alcohol collection surface, with perpetuated hydration, enables reliable capture and retention of particles, and the polyvinyl alcohol itself does not interfere with analysis by SEM, TEM or other methods.

9 Claims, 3 Drawing Sheets

DEVICE FOR COLLECTING AIRBORNE PARTICULATE SAMPLES

FIELD OF THE INVENTION

The invention relates to improved methods of passive sampling of airborne particles.

BACKGROUND OF THE INVENTION

Particle sampling is typically accomplished by either "active" or "passive" techniques. When air samples containing airborne particles are pumped through and captured onto a filter, the sampling is active. When airborne particles are allowed to settle naturally onto a collection surface, the sampling is passive. A number of materials have been used as collection surfaces, often as collection "plates," for passive sampling. These materials include carbon-coated sheets of thin mica, polycarbonate filter material, quartz crystals and glass slides.

Unfortunately, the inert surfaces typically used for passive sampling of airborne particulates inherently results in some particle loss—prior to particle analysis—in one of two ways. First, due to the nature of the collection surface and depending upon the particle size and settling or impact velocity, a particle may bounce free of the collection material. Second, because the particles are not physically fixed or held to the collection surface, they are easily dislodged and lost from the collection surface between collection and particle evaluation—particularly because, as is discussed further below, evaluation is seldom if ever conducted at the sampling site itself.

The media used for passive collection should be suitable for both optical and electron microscopy examination. Although limited by resolution and magnification, optical microscopy provides a quick and overall view of the sample without damaging the specimen. Electron microscopy provides higher resolution and magnification and in addition provides the capability of determining the chemical composition of particles by energy dispersive x-ray spectroscopy. Two methods of electron microscopy, Scanning Electron Microscopy (SEM) and Transmission Electron Microscopy (TEM) are used. The collection media should also be suitable for application of other methods of particle characterization such as x-ray diffraction (XRD) and atomic absorption (AA).

Particle deposition plates preferably should be of a type to allow direct and indirect microscopic analysis. If it is relevant to study the relative orientation and the distribution of the particles as deposited, a direct preparation method is used. With direct preparation techniques, the sample is examined in the as-received condition, i.e., directly on the collection plate. Indirect preparation for electron microscopy involves transferring the particles from the collection plate into a liquid and redepositing them onto a filter membrane to obtain a uniform distribution. The filter membrane is then prepared for electron microscopic examination, during which accurate particle concentration assessment may be made.

Conventional attempted solutions for the problem of particle loss from collection surfaces have included the use of coatings of grease or adhesive on the collection surface, and these techniques have resulted in at least some limited success. With grease or adhesives, however, the coated collection surface creates problems of sample preparation which are as serious if not more serious than the original particle loss. Without controlled tack—which is completely impossible with some adhesives and virtually all greases—the resultant sample fouling presents a worse problem than the collection problem the greases and/or adhesives were intended to solve.

The passive sampling technology therefore needs an improved method, and means for effecting the method, of collecting airborne particulates with enhanced particle capture and retention and for doing so without interfering with SEM, TEM or other methods of examination.

SUMMARY OF THE INVENTION

In order to meet this need, the present invention is a collection device in which the particle collection surface, tacky due to the presence of aqueous polyvinyl alcohol thereon, is periodically or continually hydrated, rehydrated or replenished. This perpetuated hydration of the polyvinyl alcohol collection surface prevents the loss of collection effectiveness which would occur upon dehydration of the aqueous polyvinyl alcohol to a non-tacky polymer. In one preferred embodiment of the invention, the collection surface is kept in continuous saturation with aqueous polyvinyl alcohol by means of a wick connecting the collection surface and a reservoir of water or aqueous polyvinyl alcohol. Other hydration/replenishment/rehydration arrangements are included within the scope of the invention. The polyvinyl alcohol collection surface, with perpetuated hydration, enables reliable capture and retention of particles, and the polyvinyl alcohol itself does not interfere with analysis by SEM, TEM or other methods.

DETAILED DESCRIPTION OF THE INVENTION

Basically, the present invention embraces any collection surface for airborne particulates in which 1) aqueous polyvinyl alcohol provides tack to the collection surface and 2) means are provided for the periodic or continuous replenishment, hydrating or rehydrating of the aqueous polyvinyl alcohol. A number of arrangements for accomplishing these two essential elements of the present invention are described below, but others will be readily apparent to those skilled in the art.

Figure 1:
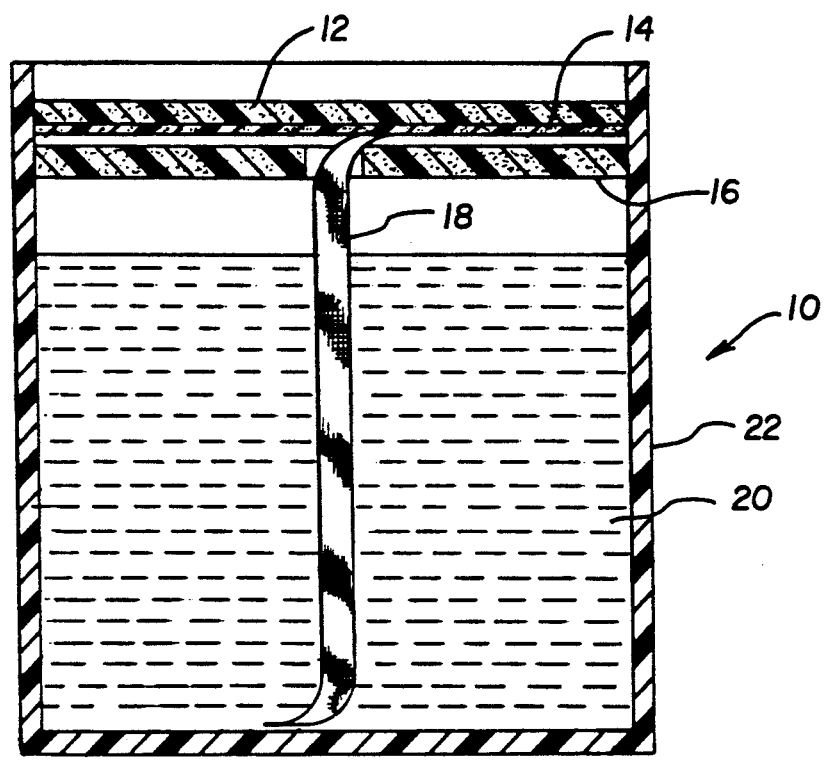
FIG. 1 is a sectional view of a collection device according to the present invention.

One way of providing aqueous polyvinyl alcohol to a collection surface, and of keeping the polyvinyl alcohol aqueous, is shown in FIG. 1. A collection device 10 includes a container 22 which includes, near its upper end, a collection surface 12. Below the collection surface 12 is a porous substrate 14. The porous substrate 14 is suspended within the container 22 by porous substrate support 16. One end of a wick 18 is in contact with the porous substrate 14 by virtue of its being sandwiched in between the porous substrate 14 and the porous substrate support 16; the other end of the wick 18 is immersed in a reservoir 20.

When the configuration according to FIG. 1 is optimally constructed, the collection surface 12 is fabricated of a filter membrane such as polycarbonate material having a fine (e.g. 0.2 micron) pore size. The porous substrate support 16 and the container 22 are generally made of rigid plastic such as polyvinyl chloride; the porous substrate 14 is made of an absorbent material such as cellulose. Any wicking material (polyester or other synthetic fiber, or natural fibers) may be used to make the wick 18. The reservoir 20 contains an aqueous solution of polyvinyl alcohol. Most preferably, the solution in the reservoir is a 1 to 6% solution of polyvinyl alcohol with 0.02% by volume sodium azide added as a growth inhibitor. Polyvinyl alcohols (87 to 89% hydrolyzed) with molecular weights of 13,000 to 23,000 and 23,000 to 46,000 have worked satisfactorily. Higher molecular weights will work also but are more difficult to dissolve in water. Polyvinyl alcohol products having these ranges are commercially available; more particulars concerning the molecular weight distribution within the range of the product is not known. As shown in FIG. 1, the reservoir itself constitutes a volume of liquid which typically terminates beneath and without contacting the porous substrate support 16.

After the collection device 10 as described according to the previous two paragraphs is assembled, it is ready for placement in the test site once the polyvinyl alcohol solution has transported up the wick 18, through the porous substrate 14 and through and onto the entirety of the collection surface 12. In use, the collection surface 12 is exposed to the air of the test site and the tacky aqueous polyvinyl alcohol coating on the collection surface 12 "holds on" to any particles which settle on it. The continuous supplying of fresh polyvinyl alcohol solution to the collection surface 12 by means of the wick 18 assures that the collection surface 12 remains moist and tacky for extended periods of collection time.

Although the collection device 10 of FIG. 1 can be used with aqueous polyvinyl alcohol solution, alone, in the reservoir, relatively long sampling times will at least sometimes support bacterial growth since polyvinyl alcohol solution is a carbon-rich medium. When it is used, the sodium azide performs a preventive of bacterial as well as fungal growth for a period of at least 30 days, but 0.02% concentration of sodium azide by volume is dilute enough that it does not foul the collected particulates for the purpose of later testing and identifying those particulates. On the other hand, when it is desired to collect airborne microorganisms, sodium azide would not be added.

In the device as illustrated in FIG. 1, three components (the wick 18, the porous substrate 14 and the collection surface 12) must all be permeable to aqueous polyvinyl alcohol. Because the present invention inheres in the maintained hydration of a polyvinyl alcohol film on a collection surface, however, the device of FIG. 1 is only one of many devices which accomplish the invention.

Figure 2:
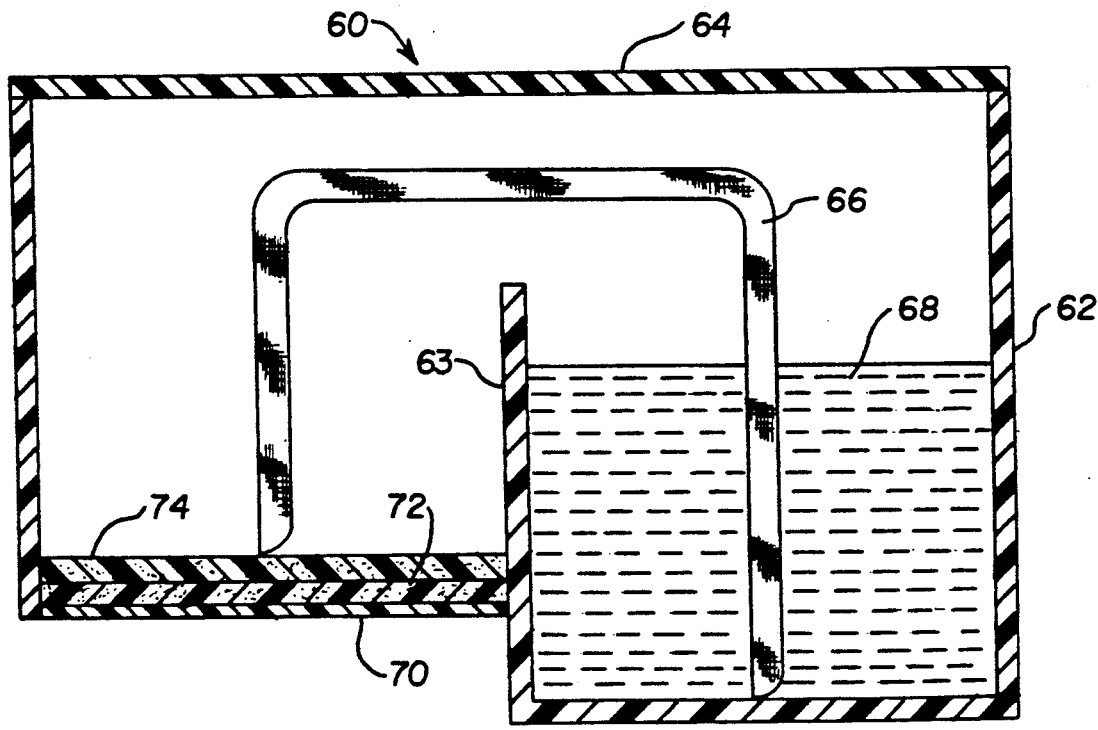
FIG. 2 is a sectional view of a second embodiment of the present collection device.

Referring now to FIG. 2, a collection device 60 is shown having greater similarity to the collection device 10 of FIG. 1 than might at first be evident. As an overview, the collection device 60 of FIG. 2 contains the same basic elements as does the collection device 10 of FIG. 1, except that wicking of the aqueous polyvinyl alcohol is done, via the wick, from above onto a first porous substrate 74 and a more finely porous second porous substrate 72, the latter of which minimizes undue permeability and possible unwanted drainage or dripping of the aqueous polyvinyl alcohol onto the filter membrane collection surface 70. This embodiment allows sampling to take place from atop a body of air, and applications which would require this sampling approach will be readily evident to those skilled in the airborne particulate sampling arts. Although the wick 66 is shown in an exaggerated position of extending up out of the reservoir 68, over the container partition 63 and down onto the second porous substrate 72, adjusting of the height of the collection surface 70 (and associated layers) relative to the level of the reservoir 68 will prevent unwanted wicking and gravitational transfer of excess aqueous polyvinyl alcohol into the area of the first and second porous substrates 74 and 72.

Figure 3:
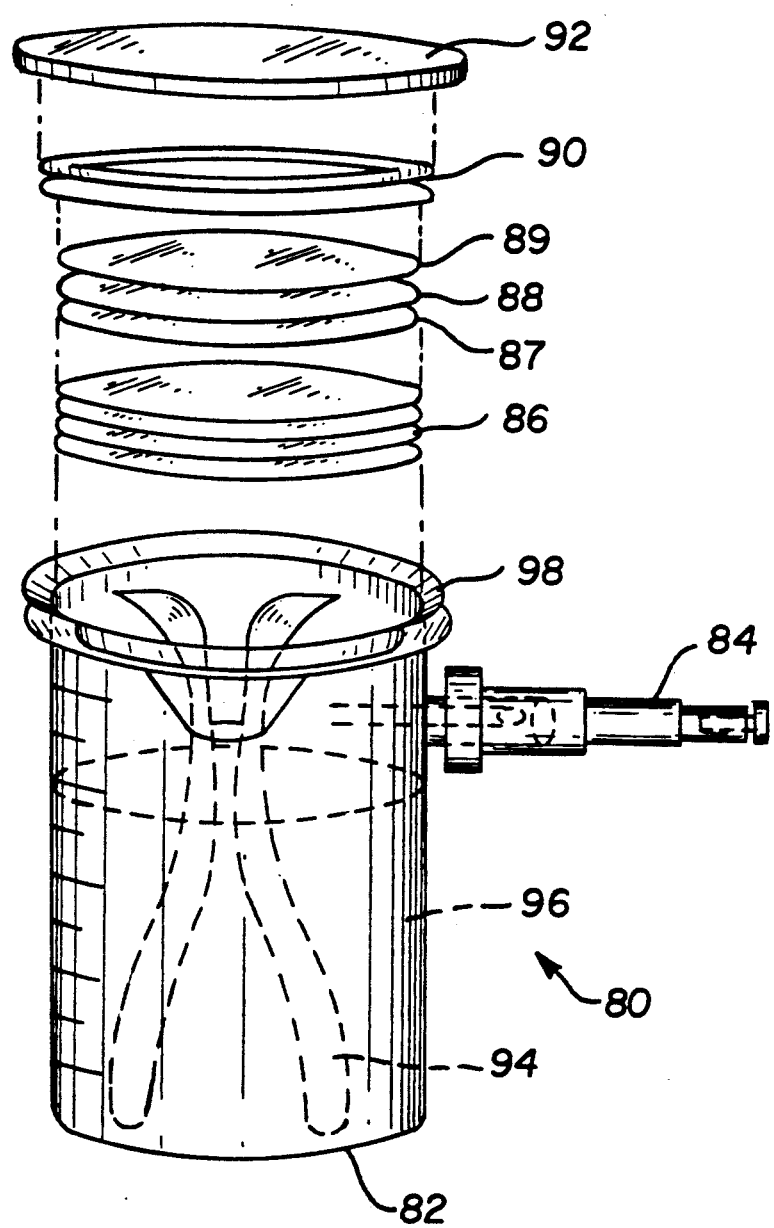
FIG. 3 is an exploded perspective view of a third embodiment of the present collection device.

FIG. 3 illustrates a slightly more elaborate version of the embodiment of FIG. 1, in which the collection device 80 has the added features of a lid (for minimizing contamination), additional filter materials and a container access port. The collection device 80 thus includes a container 82 having a container access port 84 thereon, with filter support ring 98, porous substrate 86, prefilter 27, collection filter 88, protection filter 89, lid ring 90 and lid 92 as shown. The wick 94 is double, to enhance even distribution of the aqueous polyvinyl alcohol contained within the reservoir 96. Despite the enhancements of the embodiment of FIG. 3 over the embodiment of FIG. 1, the invention remains the same: the present invention embraces any collection surface for airborne particulates in which 1) aqueous polyvinyl alcohol provides tack to the collection surface and 2) means are provided for the periodic or continuous hydrating or rehydrating the aqueous polyvinyl alcohol. Thus, the elaborate arrangement of FIG. 3 is not by any means necessary to practice the present invention.

Figure 4:
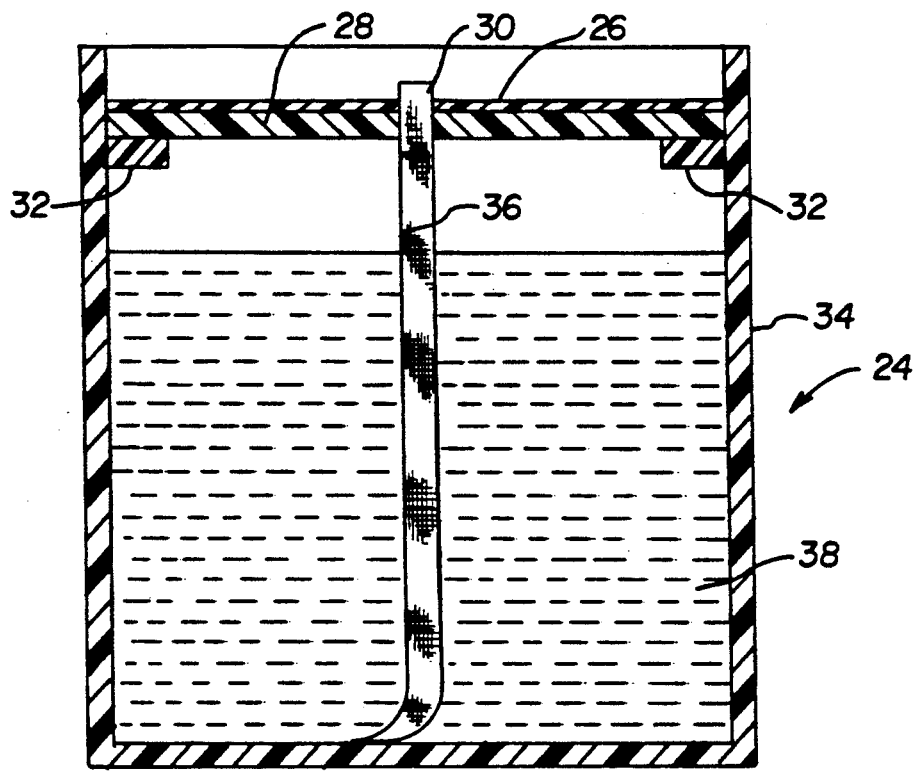
FIG. 4 is a sectional view of a fourth embodiment of the invention.

Referring now to FIG. 4, an alternate design for a collection device 24 is illustrated, in which the collection plate need not be fabricated of a material permeable to aqueous polyvinyl alcohol. The collection device 24 includes a container 34 enclosing a reservoir 38 and a wick 36. Collection plate support(s) 32 within the container 34 provide support means for a collection plate 28 near the top of the container 34. The collection plate 28 is itself impermeable to aqueous polyvinyl alcohol except via the collection plate aperture 30, shown in FIG. 4 as the wick-(36)-filled area central to the collection plate 28. The wick 36 extends slightly above the collection plate 28 and prevents dehydration of the aqueous polyvinyl alcohol coating 26 thereon. Because the wicking force is not as great in the device of FIG. 4 as it is in the device of FIG. 1, the aqueous polyvinyl alcohol coating 26 may be primed onto the collection plate 28 at the time particle collection begins; the wicking action of the wick 36 primarily acts to prevent dehydration to the coating 26. If the collection plate 28 is not primed with a coating 26, then the reservoir 38 should be filled with an aqueous solution of polyvinyl alcohol, most preferably with a 1 to 6% solution of polyvinyl alcohol having a molecular weight in the range of about 23,000 to 46,000 with 0.02% by volume sodium azide added as a growth inhibitor if necessary (see above). In this event, enough time should be provided between assembly of the collection device 24 and the onset of sampling to enable adequate wicking of ample aqueous polyvinyl alcohol to form the coating 26. If the collection plate 28 is primed with a coating 26 of aqueous polyvinyl alcohol, the reservoir may alternatively be filled merely with water, and the wicking of the water prevents dehydration of the aqueous polyvinyl alcohol coating 26 and accomplishes the desired results of the present invention. Reservoirs filled with water only may also be adapted to other embodiments of the invention.

Figure 5:
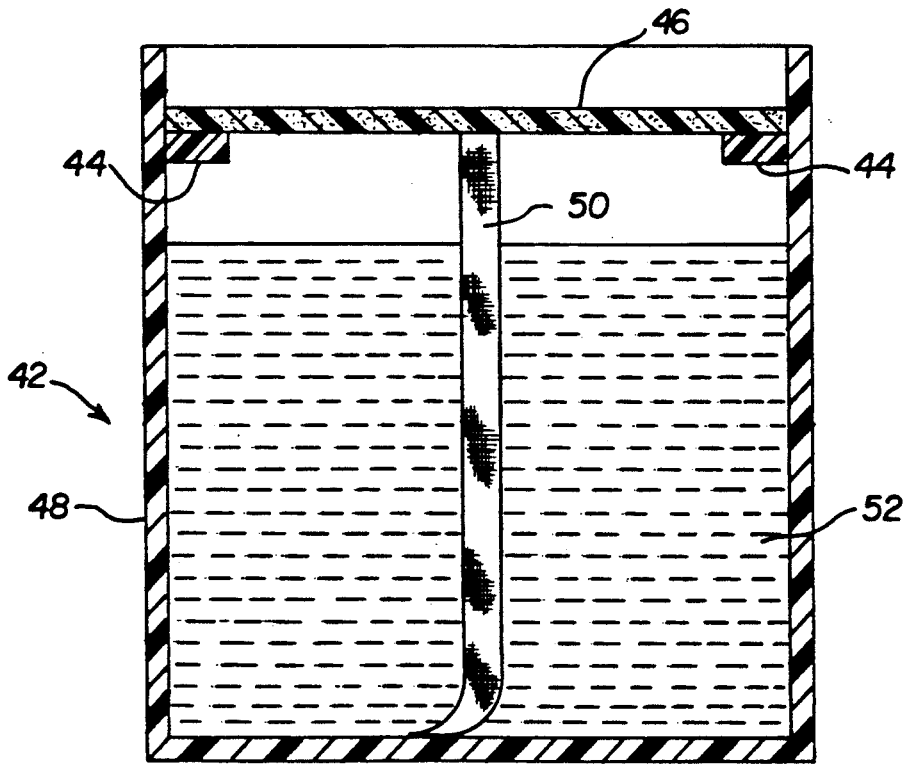
FIG. 5 is a sectional view of a fifth embodiment of the invention.

It should be evident to one skilled in the art, who considers the above descriptions and illustrations of FIGS. 1 and 4, that combinations of the various elements of FIG. 1 and FIG. 4 may be made without departing the boundaries of the invention (i.e., preventing dehydration in aqueous polyvinyl alcohol coated particle collection surfaces). One example of a collection device containing elements of both the device 10 of FIG. 1 and the device 24 of FIG. 4 is shown in FIG. 5. FIG. 5 illustrates a collection device 42 including a container 48, collection material support(s) 44, collection material 46, a wick 50 and a reservoir 52 in which the wick 50 is attached directly to the collection material 46 upon which particles are collected. As in the device 10 of FIG. 1, the collection material 46 of FIG. 5 is made of a material permeable to aqueous polyvinyl alcohol. In fact, the material selected is sufficiently permeable (for example, a cellulosic material) to aqueous polyvinyl alcohol that the porous substrate 14 of FIG. 1 is not necessary. The wick 50 and the collection material are connected by any means known in the art: press fit, slot-and-loop, stitching or any chemical or physical bonding agents which do not interfere with wicking of the aqueous polyvinyl alcohol from the reservoir 52 through the wick 50 and into and through the collection material 46.

In view of the foregoing, it may be seen that the present invention is entirely different in both concept and specific feature from the tape disclosed in U.S. Pat. No. 4,144,760 to Schlueter et al. Schlueter et al. disclose a sample collection tape, but the samples contemplated do not have to do with airborne particles. Instead, the Schlueter et al. device is a tape for taking up samples such as cell samples from a urethra or tear duct or other difficult to reach area, or for taking samples during a gynecological exam, or for taking soil samples, or surface germ samples in the food industry, or for collecting fiber samples in criminal investigations, etc. In other words, the Schlueter et al. device is designed for contacting onto a sample or surface to be studied, after which the device is removed with a sample adhered thereto. Schlueter et al. disclose the use of a tape having a polyvinyl alcohol coating thereon, and the coating is contacted with water prior to application of the tape to the sample surface. The tape is immediately removed after application to the sample surface, and the sampled material is prepared for further testing. In addition to the different concept and application of the tape of Schlueter et al., therefore, there is no disclosure or suggestion whatever of the present inventive periodic or continuous rehydration of a polyvinyl alcohol collection surface, the aspect of the invention which has been repeatedly emphasized above.

Other configurations not illustrated may be derived to implement the concept of the invention. It is contemplated, for example, that a remote spraying of the collection surface is not outside the bounds of possibility for the periodic or continuous rehydration of a polyvinyl alcohol collection surface. Such spraying (or misting) would have to be conducted in such a way so as not to interfere with the airborne particulates being studied, but one skilled in the art would not find this design consideration to pose much if any of a problem. Also, wicks may be introduced into the sides of the collection surfaces or associated structures, even though the figures show wicks extending to the collection surface from either above or beneath the collection surface. Finally, although the invention is largely directed specifically to the use of polyvinyl alcohol as the polymer which tackifies upon hydration and yet which does not foul the sample for analysis purposes, it is believed that those skilled in the art will readily determine chemical equivalents to the aqueous polyvinyl alcohol and these equivalents are understood by the inventors to come within the scope of the claimed invention.

The invention will be more readily understood by the illustration afforded in the following examples.

EXAMPLE 1

In the initial studies, a 6% solution of 23,000 to 46,000 molecular weight polyvinyl alcohol in water was used with polycarbonate filters in a variety of ways to determine whether airborne particulates could be collected. For example, in one experiment, a polycarbonate filter was floated on the surface of a polyvinyl alcohol solution contained in a petri dish. When the filter became wetted by the polyvinyl alcohol, the assembly was placed in a location to collect particles from the atmosphere. In another experiment, a polycarbonate filter was simply soaked in polyvinyl alcohol solution prior to locating it for particle collection. After being exposed to the atmosphere for a period of time, the filters were removed from the collection sites and were prepared for electron microscopic examination. This examination showed that indeed the polyvinyl alcohol had captured particulate material that had settled from the air, that the adhesive characteristics of the PVA had "locked" such particles in place, and that the particles could be readily examined and analyzed. The second trial confirmed that the latter methodology permitted only the relatively short term collection of airborne particles, because the polyvinyl alcohol solution lost its tack after about 24 hours.

EXAMPLE 2

The collection device 10 of FIG. 1 was provided with a reservoir 20 of a 6% aqueous solution of 23,000 to 46,000 molecular weight of polyvinyl alcohol. This 23,000 to 46,000 molecular weight polyvinyl alcohol polymer was commercially obtained and the molecular weight distribution was unknown. The amount of 0.02% by volume sodium azide was added to the solution to inhibit bacterial and fungal growth. The polyvinyl alcohol solution wicked up the wick 18, wicked through the porous substrate 14 and saturated the collection surface 12. At this point, the collection device 10 was placed in the test area. After 30 days, it was observed in the test area that the collection surface 12 was still moist and tacky. The collection surface 12 was capped and the device was transported to a laboratory. At the laboratory, the collection surface 12 was removed from the device, dried, and sections of it were prepared for direct examination by scanning electron microscopy (SEM) using standard procedures. The sections were mounted on a SEM sample holder or stub for examination in the SEM. In some cases where relatively high beam currents were used, damage to the polyvinyl alcohol film interfered somewhat with the examination and in these instances the polyvinyl alcohol was carefully leached from the sections as follows.

First, the sections were placed atop porous substrates saturated with water containing a wetting agent known in the art, such as Liqui Nox, and were permitted to stand undisturbed for 30 minutes. The sections were then transferred to different porous substrates saturated with water for an additional 30 minutes. Finally, a vacuum filtration device was used to aspirate the now highly dilute polyvinyl alcohol from the non-particulate side of the section, and the section was carefully dried (without dislodging particles) and prepared for examination.

EXAMPLE 3

The collection device 10 of FIG. 1 was provided with a reservoir 20 of 6% polyvinyl alcohol solution (aqueous), the molecular weight of the polyvinyl alcohol was 23,000 to 46,000. The amount of 0.02% by volume sodium azide was added to the solution to inhibit bacterial and fungal growth. The polyvinyl alcohol solution wicked up the wick 18, wicked through the porous substrate 14 and saturated the collection surface 12. At this point, the collection device 10 was placed in the test area. After 30 days, it was observed in the test area that the collection surface 12 was still moist and tacky. The collection surface 12 was capped and the device was transported to a laboratory. At the laboratory, the collection surface 12 was prepared for examination as follows: The collection surface 12 was removed from the device 10 and was submerged in water containing a wetting agent and was gently agitated with ultrasound. In this way, the polyvinyl alcohol was dissolved and the particles were released into the solution. Then, according to procedures known in the art, the suspended particles were redeposited onto a new filter of desired type and pore size. The filter was allowed to dry and was prepared for examination by means known in the art.

EXAMPLE 4

Optical, SEM and TEM examination of a substantial number of samples collected in accordance with Examples 2 and 3 above demonstrated that the present collection device is highly effective in collecting airborne particles.

CONCLUSION

Although the invention has been described with particularity above, it is only intended to be limited insofar as is set forth in the accompanying claims.

We claim:

1. A particle collection device comprising: a container having therewithin a particle collection surface, said surface having a quantity of aqueous polyvinyl alcohol adjacent and adhered thereto, wherein said container is provided with means for rehydrating said quantity of aqueous polyvinyl alcohol, wherein said means for rehydrating assures that the collection surface remains moist and tacky for extended periods of collection time.

2. The particle collection device as set forth in claim 1, wherein said means for rehydrating said quantity of aqueous polyvinyl alcohol further comprises means for periodically rehydrating said quantity of aqueous polyvinyl alcohol.

3. The particle collection device as set forth in claim 1, wherein said means for rehydrating said quantity of aqueous polyvinyl alcohol further comprises means for continuously rehydrating said quantity of aqueous polyvinyl alcohol.

4. The particle collection device as set forth in claim 1, wherein said container contains said means for rehydrating, said means further comprising a reservoir of aqueous polyvinyl alcohol solution, a porous substrate support, a porous substrate, and a wick, said porous substrate being positioned adjacent said particle collection surface and said particle collection surface being porous.

5. The particle collection device as set forth in claim 4, wherein said wick extends from within said reservoir to a position adjacent said collection surface.

6. The particle collection device as set forth in claim 5, wherein said device is further provided with a removable lid.

7. The particle collection device as set forth in claim 6, wherein said wick further comprises a double wick.

8. The method for collecting airborne particle samples, comprising providing a collection surface within a container wetting said collection surface with a quantity of an aqueous polyvinyl alcohol and, rehydrating said aqueous polyvinyl alcohol, whereby said aqueous polyvinyl alcohol retains its tack for extended periods of collection time and effectively collects airborne particles which settle thereon.

9. The method for collecting airborne particle samples according to claim 8, wherein said method further comprises wetting a collection surface with a quantity of an aqueous polyvinyl alcohol solution, by transferring said solution from a reservoir by means of a wick, to form an aqueous polyvinyl alcohol film and continuously rehydrating said aqueous polyvinyl alcohol film whereby said aqueous polyvinyl alcohol film retains its tack and effectively collects airborne particles which settle thereon.

* * * * *